(12) United States Patent
Ceresa et al.

(10) Patent No.: US 9,877,901 B2
(45) Date of Patent: Jan. 30, 2018

(54) ORAL CARE COMPOSITION

(71) Applicant: GABA International Holding AG, Therwil (CH)

(72) Inventors: Alan Carlo Ceresa, Allschwil (CH); Rene Heckendorn, Basel (CH)

(73) Assignee: COLGATE-PALMOLIVE COMPANY, New York, NY (US)

(*) Notice: Subject to any disclaimer, the term of this patent is extended or adjusted under 35 U.S.C. 154(b) by 142 days.

(21) Appl. No.: 14/654,930

(22) PCT Filed: Dec. 24, 2012

(86) PCT No.: PCT/EP2012/076870
§ 371 (c)(1),
(2) Date: Jun. 23, 2015

(87) PCT Pub. No.: WO2014/101933
PCT Pub. Date: Jul. 3, 2014

(65) Prior Publication Data
US 2015/0335540 A1 Nov. 26, 2015

(51) Int. Cl.
| | |
|---|---|
| *A61K 8/20* | (2006.01) |
| *A61K 8/69* | (2006.01) |
| *A61K 8/21* | (2006.01) |
| *A61Q 11/00* | (2006.01) |
| *B65B 3/00* | (2006.01) |
| *A61K 8/19* | (2006.01) |

(52) U.S. Cl.
CPC .................. *A61K 8/20* (2013.01); *A61K 8/19* (2013.01); *A61K 8/21* (2013.01); *A61K 8/69* (2013.01); *A61Q 11/00* (2013.01); *B65B 3/00* (2013.01); *A61K 2800/30* (2013.01); *A61K 2800/43* (2013.01); *A61K 2800/48* (2013.01); *A61K 2800/87* (2013.01)

(58) Field of Classification Search
USPC .............................. 222/107; 401/143; 424/52
See application file for complete search history.

(56) References Cited

U.S. PATENT DOCUMENTS

| | | | | |
|---|---|---|---|---|
| 3,652,174 | A | * | 3/1972 | Boone ...................... A47K 5/04 118/325 |
| 4,626,456 | A | * | 12/1986 | Farrell .................... B32B 27/20 222/107 |
| 4,705,680 | A | | 11/1987 | Vellekoop |
| 4,970,065 | A | * | 11/1990 | Suhonen .................. A61K 8/21 424/52 |
| 5,009,883 | A | | 4/1991 | Suhonen |
| 5,009,884 | A | | 4/1991 | Suhonen |
| 5,091,182 | A | | 2/1992 | Ong et al. |
| 6,086,856 | A | | 7/2000 | Saferstein et al. |
| 6,113,885 | A | | 9/2000 | Pipes et al. |
| 2004/0022747 | A1 | * | 2/2004 | Fisher ...................... A61K 8/19 424/52 |
| 2006/0134020 | A1 | * | 6/2006 | Robinson ............. A61K 8/0216 424/52 |
| 2008/0274066 | A1 | | 11/2008 | Montgomery |

FOREIGN PATENT DOCUMENTS

WO WO 2011/124659 10/2011

OTHER PUBLICATIONS

International Search Report and Written Opinion for International Application No. PCT/EP2012/076870 dated Oct. 10, 2013.

* cited by examiner

*Primary Examiner* — Walter Webb

(57) ABSTRACT

The present application provides a packaged aqueous oral care composition comprising a container and a composition wherein the composition comprises at least one water-soluble source of $Sn^{2+}$ ions and the container comprises an inner surface being at least partially formed from a linear polymer, wherein the linear polymer is a homopolymer or a copolymer of monomers having the structure: wherein $R_1$ and $R_2$ are the same or different and are independently selected from a hydrogen atom, an alkyl group, an alkenyl group, a halogen atom and a nitrile group.

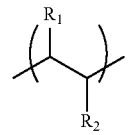

56 Claims, No Drawings

ORAL CARE COMPOSITION

BACKGROUND OF THE INVENTION

Metal ions such as stannous ($Sn^{2+}$) and zinc ions are known to be effective anti-microbial agents. These metal ions provide anti-gingivitis and anti-plaque benefits and may also improve breath and reduce sensitivity. Stannous fluoride (SnF2) has been used in dentistry since the 1950's as a fluoride source to prevent dental caries.

However, it has been observed that aqueous solutions of stannous fluoride tend to precipitate water-insoluble stannic oxide ($SnO_2$) upon aging. After a storage time of several months, such solutions may exhibit turbidity, which is believed to be due to the presence of very small crystals of stannic oxide dispersed in the solution, and the solutions may even form a sediment of stannic oxide at the bottom of the storage container. The precipitation of water-insoluble stannic oxide reduces the availability and therefore the therapeutic efficacy of the stannous ions in the oral care composition. It is believed that the precipitated water-insoluble stannic oxide has negligible or even no direct therapeutic effect.

The inclusion of chelating agents in aqueous solutions of stannous fluoride has been found to reduce the formation of this turbidity to some extent, but is also believed to impair the efficacy of the stannous ions.

Therefore, a need still exists for oral care compositions in which the bioavailability and therapeutic efficacy of the tin ions (stannous/stannic ions) is preserved, and which compositions do not exhibit turbidity upon aging.

SUMMARY OF THE INVENTION

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

A first aspect of the present invention provides a packaged aqueous oral care composition comprising a container and a composition wherein the composition comprises at least one water-soluble source of $Sn^{2+}$ ions and the container comprises an inner surface being at least partially formed from a linear polymer, wherein the linear polymer is a homopolymer or a copolymer of monomers having the structure:

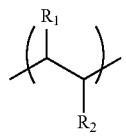

wherein $R_1$ and $R_2$ are the same or different and are independently selected from a hydrogen atom, an alkyl group, an alkenyl group, a halogen atom and a nitrile group.

Optionally, the inner surface has a smoothness adapted so as not to form a precipitation or crystallisation site for $SnO_2$.

Optionally, the halogen atom is a chlorine atom.

Optionally, the alkyl group is a $C_1$-$C_{10}$ alkyl group. Further optionally, the alkyl group is a $C_3$-$C_8$ alkyl group.

Optionally, the alkyl group is a methyl group, an ethyl group, a propyl group, a butyl group, a pentyl group or a hexyl group.

Optionally, the alkenyl group is a $C_2$-$C_{10}$ alkenyl group, optionally wherein the alkenyl group is a $C_4$-$C_8$ alkenyl group.

Optionally, $R_1$ is a hydrogen atom.

Optionally, the polymer is a homopolymer or copolymer of one or more olefins.

Optionally, the polymer is polypropylene.

Optionally, the polymer is polyethylene.

Optionally, the polymer is polyvinylchloride.

Optionally, the polymer is polyacrylonitrile.

Optionally, the $Sn^{2+}$ ions are present in the composition in a concentration of from 100 ppm to 12,000 ppm.

Optionally, the $Sn^{2+}$ ions are present in the composition in a concentration of from 400 ppm to 6,000 ppm.

Optionally, the $Sn^{2+}$ ions are present in the composition in a concentration of from 700 ppm to 4,000 ppm.

Optionally, the $Sn^{2+}$ ions are present in the composition in an amount of from 1,000 ppm to 2,000 ppm.

Optionally, the source of $Sn^{2+}$ ions comprises $SnCl_2$.

Optionally, the source of $Sn^{2+}$ ions comprises $SnF_2$.

Optionally, the composition further comprises an amine fluoride.

Optionally, the amine fluoride is N'-octadecyltrimethylendiamine-N,N,N-tris(2-ethanol)-dihydrofluoride.

Optionally, the total concentration of $F^-$ ions in the oral care composition is from 150 ppm to 5,000 ppm.

Optionally, the total concentration of $F^-$ ions present in the composition is from 200 ppm to 1,500 ppm.

Optionally, the oral care composition further comprises one or more agents selected from diluents, bicarbonate salts, pH modifying agents, surfactants, foam modulators, thickening agents, viscosity modifiers, humectants, sweeteners, flavorants, pigments, antibacterial agents, anticaries agents, anticalculus or tartar control agents, and mixtures thereof.

Optionally, the composition is free of abrasives.

Optionally, the composition comprises greater than 90 wt % water.

Optionally, the composition is a mouthrinse, an oral care liquid or a tooth gel.

Optionally, the composition has a pH of from 3 to 7. Further, optionally, the composition has a pH of from 4 to 5.

Optionally, the container is a bottle, a tube, a vial, a cartridge, a pump-action dispensing container.

In a second aspect, the present invention provides a method of preventing the formation of insoluble SnO2 in an aqueous composition comprising at least one water-soluble source of $Sn^{2+}$ ions, the method comprising packaging the aqueous composition in a container having an inner surface, wherein the inner surface is at least partially formed from a linear polymer, wherein the linear polymer is a homopolymer or a copolymer of monomers having the structure:

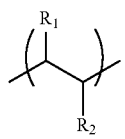

wherein $R_1$ and $R_2$ are the same or different and are independently selected from a hydrogen atom, an alkyl group, an alkenyl group, a halogen atom and a nitrile group.

Optionally, the inner surface has a smoothness adapted so as not to form a precipitation or crystallisation site for $SnO_2$.

Optionally, the halogen atom is a chlorine atom.

Optionally, the alkyl group is a $C_1$-$C_{10}$ alkyl group. Further optionally, the alkyl group is a $C_3$-$C_8$ alkyl group.

Optionally, the alkyl group is a methyl group, an ethyl group, a propyl group, a butyl group, a pentyl group or a hexyl group.

Optionally, the alkenyl group is a $C_2$-$C_{10}$ alkenyl group, optionally wherein the alkenyl group is a $C_4$-$C_8$ alkenyl group.

Optionally, $R_1$ is a hydrogen atom.

Optionally, the polymer is a homopolymer or copolymer of one or more olefins.

Optionally, the polymer is polypropylene.

Optionally, the polymer is polyethylene.

Optionally, the polymer is polyvinylchloride.

Optionally, the polymer is polyacrylonitrile.

Optionally, the $Sn^{2+}$ ions are present in the composition in a concentration of from 100 ppm to 12,000 ppm.

Optionally, the $Sn^{2+}$ ions are present in the composition in a concentration of from 400 ppm to 6,000 ppm.

Optionally, the $Sn^{2+}$ ions are present in the composition in a concentration of from 700 ppm to 4,000 ppm.

Optionally, the $Sn^{2+}$ ions are present in the composition in an amount of from 1,000 ppm to 2,000 ppm.

Optionally, the source of $Sn^{2+}$ ions comprises $SnCl_2$.

Optionally, the source of $Sn^{2+}$ ions comprises $SnF_2$.

Optionally, the composition further comprises an amine fluoride.

Optionally, the amine fluoride is N'-octadecyltrimethyl-endiamine-N,N,N-tris(2-ethanol)-dihydrofluoride.

Optionally, the total concentration of $F^-$ ions in the composition is from 150 ppm to 5,000 ppm.

Optionally, the total concentration of $F^-$ ions present in the composition is from 200 ppm to, 500 ppm.

Optionally, the composition further comprises one or more agents selected from diluents, bicarbonate salts, pH modifying agents, surfactants, foam modulators, thickening agents, viscosity modifiers, humectants, sweeteners, flavorants, pigments, antibacterial agents, anticaries agents, anticalculus or tartar control agents, and mixtures thereof.

Optionally, the composition is free of abrasives.

Optionally, the composition comprises greater than 90 wt % water.

Optionally, the composition is an oral care composition.

Optionally, the composition is a mouthrinse, an oral care liquid or a tooth gel.

Optionally, the composition has a pH of from 4 to 5.

Optionally, the container is a bottle, a tube, a vial, a cartridge, a pump-action dispensing container.

In a third aspect, the present invention provides for use of a container having an inner surface which is at least partially formed from a linear polymer, wherein the linear polymer is a homopolymer or a copolymer of monomers having the structure:

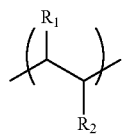

wherein $R_1$ and $R_2$ are the same or different and are independently selected from a hydrogen atom, an alkyl group, an alkenyl group, a halogen atom and a nitrile group, for preventing the formation of insoluble $SnO_2$ in an aqueous composition comprising at least one water-soluble source of $Sn^{2+}$ ions when the aqueous composition is packaged in the container.

Optionally, the inner surface has a smoothness adapted so as not to form a precipitation or crystallisation site for $SnO_2$.

Optionally, the halogen atom is a chlorine atom.

Optionally, the alkyl group is a $C_1$-$C_{10}$ alkyl group. Further optionally, the alkyl group is a $C_3$-$C_8$ alkyl group.

Optionally, the alkyl group is a methyl group, an ethyl group, a propyl group, a butyl group, a pentyl group or a hexyl group.

Optionally, the alkenyl group is a $C_2$-$C_{10}$ alkenyl group, optionally wherein the alkenyl group is a $C_4$-$C_8$ alkenyl group.

Optionally, $R_1$ is a hydrogen atom.

Optionally, the polymer is a homopolymer or copolymer of one or more olefins.

Optionally, the polymer is polypropylene.

Optionally, the polymer is polyethylene.

Optionally, the polymer is polyvinylchloride.

Optionally, the polymer is polyacrylonitrile.

Optionally, the $Sn^{2+}$ ions are present in the composition in a concentration of from 100 ppm to 12,000 ppm.

Optionally, the $Sn^{2+}$ ions are present in the composition in a concentration of from 400 ppm to 6,000 ppm.

Optionally, the $Sn^{2+}$ ions are present in the composition in a concentration of from 700 ppm to 4,000 ppm.

Optionally, the $Sn^{2+}$ ions are present in the composition in an amount of from 1,000 ppm to 2,000 ppm.

Optionally, the source of $Sn^{2+}$ ions comprises $SnCl_2$.

Optionally, the source of $Sn^{2+}$ ions comprises $SnF_2$.

Optionally, the composition further comprises an amine fluoride.

Optionally, the amine fluoride is N'-octadecyltrimethyl-endiamine-N,N,N'-tris(2-ethanol)-dihydrofluoride.

Optionally, the total concentration of $F^-$ ions in the composition is from 150 ppm to 5,000 ppm.

Optionally, the total concentration of $F^-$ ions present in the composition is from 200 ppm to 1,500 ppm.

Optionally, the composition further comprises one or more agents selected from diluents, bicarbonate salts, pH modifying agents, surfactants, foam modulators, thickening agents, viscosity modifiers, humectants, sweeteners, flavorants, pigments, antibacterial agents, anticaries agents, anticalculus or tartar control agents, and mixtures thereof.

Optionally, the composition is free of abrasives.

Optionally, the composition comprises greater than 90 wt % water.

Optionally, the composition is an oral care composition.

Optionally, the composition is a mouthrinse, an oral care liquid or a tooth gel.

Optionally, the composition has a pH of from 3 to 7. Further, optionally, the composition has a pH of from 4 to 5.

Optionally, the container is a bottle, a tube, a vial, a cartridge, a pump-action dispensing container.

DETAILED DESCRIPTION OF THE PREFERRED EMBODIMENTS

The following description of the preferred embodiment(s) is merely exemplary in nature and is in no way intended to limit the invention, its application, or uses.

As referred to herein, all compositional percentages are by weight of the total composition unless otherwise indicated. As referred to herein, "ppm" (parts per million) refers to ppm by weight, unless otherwise indicated. As referred to herein, all ratios refer to weight ratios, unless otherwise indicated.

In some embodiments, the present invention provides a packaged aqueous oral care composition comprising a container and a composition wherein the composition comprises at least one water-soluble source of $Sn^{2+}$ ions and the container comprises an inner surface being at least partially formed from a linear polymer, wherein the linear polymer is a homopolymer or a copolymer of monomers having the structure:

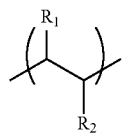

wherein $R_1$ and $R_2$ are the same or different and are independently selected from a hydrogen atom, an alkyl group, an alkenyl group, a halogen atom and a nitrile group.

Linear Polymer

A linear polymer as used in the context of the present invention is a homopolymer or a copolymer of monomers having the structure:

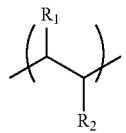

wherein $R_1$ and $R_2$ are the same or different and are independently selected from a hydrogen atom, an alkyl group, an alkenyl group, a halogen atom and a nitrile group.

As used herein, a halogen atom may be a fluorine atom, a chlorine atom, a bromine atom or an iodine atom. In some embodiments, the halogen atom is a chlorine atom.

In some embodiments, the alkyl group is a $C_1$-$C_{10}$ alkyl group. The alkyl group may be a $C_3$-$C_8$ alkyl group, or may be a $C_4$-$C_6$ alkyl group. In some embodiments, the alkyl group is a methyl group, an ethyl group, a propyl group, a butyl group, a pentyl group or a hexyl group. The propyl group may be an n-propyl group or an isopropyl group. The butyl group may be an n-butyl group, an isobutyl group, a sec-butyl group, or a tert-butyl group.

In some embodiments, the alkenyl group is a $C_2$-$C_{10}$ alkenyl group. The alkenyl group may be a $C_4$-$C_8$ alkenyl group.

In some embodiments, $R_1$ is a hydrogen atom.

Typically, the polymer is a homopolymer or copolymer of one or more olefins.

In some embodiments, the polymer is polypropylene. In some embodiments, the polymer is polyethylene. In some embodiments, the polymer is polyvinylchloride. In some embodiments, the polymer is polyacrylonitrile.

Aqueous Composition

The compositions of the present invention are aqueous compositions comprising at least one water-soluble source of $Sn^{2+}$ ions (stannous ions).

In those embodiments where the aqueous composition is an oral care composition, the composition may be a mouthrinse, an oral care liquid or a tooth gel.

In some embodiments, the $Sn^{2+}$ ions are present in the composition in a concentration of from 100 ppm to 12,000 ppm.

In some embodiments, the $Sn^{2+}$ ions are present in the composition in a concentration of from 400 ppm to 6,000 ppm.

In some embodiments, the $Sn^{2+}$ ions are present in the composition in a concentration of from 700 ppm to 4,000 ppm.

In some embodiments, the $Sn^{2+}$ ions are present in the composition in an amount of from 1,000 ppm to 2,000 ppm.

In some embodiments, the source of $Sn^{2+}$ ions comprises $SnF_2$ (stannous fluoride). In some embodiments, the source of $Sn^{2+}$ ions comprises $SnCl_2$ (stannous chloride). In some embodiments, the composition has a pH of from 3 to 7. In some embodiments, the composition has a pH of from 4 to 5.

In some embodiments, the composition also comprises an amine fluoride. In some embodiments, the amine fluoride is N'-octadecyltrimethylendiamine-N,N,N'-tris(2-ethanol)-dihydrofluoride (OLAFLUR).

In some embodiments, the total concentration of $F^-$ ions in the composition is from 150 ppm to 5,000 ppm.

In some embodiments, the total concentration of $F^-$ ions present in the composition is from 200 ppm to 1,500 ppm.

In one embodiment where the composition is a mouthrinse, the composition comprises the amine fluoride N'-octadecyltrimethylendiamine-N,N,N'-tris(2-ethanol)-dihydrofluoride in an amount corresponding to 125 ppm fluoride and stannous fluoride ($SnF_2$) in an amount also corresponding to 125 ppm fluoride. One such composition is meridol® mouthrinse, available from GABA International.

In some embodiments, the oral care compositions may comprise one or more agents selected from diluents, bicarbonate salts, pH modifying agents, surfactants, foam modulators, thickening agents, viscosity modifiers, humectants, sweeteners, flavorants, pigments, antibacterial agents, anticaries agents, anticalculus or tartar control agents, and mixtures thereof.

The compositions of the present invention are aqueous compositions. In those embodiments wherein the composition is a mouthrinse, water may be included in the composition in an amount of greater than 90 wt %, or from 10 wt % to 90 wt %, optionally 30 wt % to 80 wt %, further optionally 25 wt % to 75 wt %. In those embodiments wherein the composition is a mouthrinse, the composition may also comprise an alcohol, e.g., ethanol. The weight ratio of water to alcohol in a mouthrinse composition is typically 1:1 to 20:1, for example 3:1 to 20:1 or 4:1 to 10:1.

In some embodiments, the composition is free of abrasives.

In some embodiments, the composition has a pH of from 3 to 7. In some embodiments, the composition has a pH of from 4 to 5.

In some embodiments, the oral care compositions of the present invention comprise at least one bicarbonate salt, useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. One or more bicarbonate salts are optionally present in a total amount of 0.1 wt. % to 50 wt. %, for example 1 wt. % to 20 wt. %, by total weight of the composition.

In some embodiments, the compositions of the present invention comprise at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

In a still further embodiment, the compositions of the invention comprise at least one surfactant. Any orally acceptable surfactant, most of which are anionic, nonionic or amphoteric, can be used. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of 0.01 wt % to 10 wt. %, for example, from 0.05 wt. % to 5 wt. %, or from 0.1 wt. % to 2 wt. % by total weight of the composition.

In some embodiments, the compositions of the invention comprise at least one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000,000, for example 500,000 to 5,000,000, or 1,000,000 to 2,500,000. One or more PEGs are optionally present in a total amount of 0.1 wt. % to 10 wt. %, for example from 0.2 wt. % to 5 wt. %, or from 0.25 wt. % to 2 wt %, by total weight of the composition.

In some embodiments, the compositions of the present invention comprise at least one thickening agent, useful for example to impart a desired consistency and/or mouth feel to the composition. Any orally acceptable thickening agent can be used, including without limitation, carbomers, also known as carboxyvinyl polymers, carrageenans, also known as Irish moss and more particularly i-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, 974P, and mixtures thereof. One or more thickening agents are optionally present in a total amount of from 0.01 wt. % to 15 wt %, for example from 0.1 wt % to 0 wt %, or from 0.2 wt % to 5 wt %, by total weight of the composition.

In some embodiments, the compositions of the invention comprise at least one viscosity modifier, useful for example to inhibit settling or separation of ingredients or to promote re-dispersibility upon agitation of a liquid composition. Any orally acceptable viscosity modifier can be used, including without limitation, mineral oil, petrolatum, clays and organomodified clays, silica and the like. One or more viscosity modifiers are optionally present in a total amount of from 0.01 wt. % to 10 wt. %, for example, from 0.1 wt % to 5 wt %, by total weight of the composition.

In some embodiments, the compositions of the invention comprise at least one humectant. Any orally acceptable humectant can be used, including without limitation, polyhydric alcohols such as glycerin, sorbitol, xylitol or low molecular weight PEGs. Most humectants also function as sweeteners. One or more humectants are optionally present in a total amount of from 1 wt % to 70 wt %, for example, from 1 wt % to 50 wt %, from 2 wt % to 25 wt %, or from 5 wt % to 15 wt %, by total weight of the composition.

In some embodiments, a composition of the present invention comprises at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount depending strongly on the particular sweetener(s) selected, but typically 0.005 wt % to 5 wt %, by total weight of the composition, optionally 0.005 wt % to 0.2 wt %, further optionally 0.05 wt % to 0.1 wt % by total weight of the composition.

In some embodiments, a composition of the present invention comprises at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from 0.01 wt. % to 5 wt. %, for example, from 0.03 wt. % to 2.5 wt %, optionally 0.05 wt % to 1.0 wt %, further optionally 0.1 wt % to 0.3 wt % by total weight of the composition.

A composition of the invention may comprise at least one colorant. Colorants herein include pigments, dyes, lakes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of from 0.001 wt % to 20 wt %, for example, from 0.01 wt % to 10 wt. %, or from 0.1 wt. % to 5 wt %, by total weight of the composition.

The compositions of the present invention optionally comprise an antibacterial or preservative agent, such as chlorhexidine, triclosan, quaternary ammonium compounds (for example benzalkonium chloride) or parabens such as methylparaben or propylparaben. One or more antibacterial or preservative agent is optionally present in the composition in a total amount of from 0.01 wt % to 0.5 wt %, optionally 0.05 wt % to 0.1 wt % by total weight of the composition.

The composition of the present invention optionally comprises a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The composition of the present invention optionally incorporates one or more antisensitivity agents, e.g., potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from 1 wt. % to 20 wt. % by weight based on the total weight of the composition, depending on the agent chosen. The compositions of the present invention may also be used to treat hypersensitivity by blocking dentin tubules when applied to a tooth.

In some embodiments, the composition of the invention further comprises an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

In another embodiment, the composition comprises an orally acceptable zinc ion source useful, for example, as an antimicrobial, anticalculus or breath-freshening agent. One or more such sources can be present. Suitable zinc ion sources include without limitation zinc acetate, zinc citrate, zinc gluconate, zinc glycinate, zinc oxide, zinc sulfate, sodium zinc citrate and the like. One or more zinc ion sources are optionally and illustratively present in a total amount of from 0.05 wt % to 3 wt %, for example from 0.1 wt. % to 1 wt %, by total weight of the composition.

The composition of the present invention may additionally optionally comprise a tartar control (anticalculus) agent as provided below. Tartar control agents among those useful herein include salts of the specified agents, including alkali metal and ammonium salts. The agents include: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-disphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

In some embodiments, the composition of the present invention further comprises a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophan, L-lysine, methionine, threonine, levocarnitine and L-carnitine), lipotropics (such as choline, inositol, betaine, and linoleic acid), and mixtures thereof.

Container

In the present invention, the container has an inner surface, wherein the inner surface is at least partially formed from any of the linear polymers as described above.

In some embodiments, the container is a bottle, a tube, a vial, a cartridge, a pump-action dispensing container.

In some embodiments, the inner surface of the container is entirely formed from any of the linear polymers as described above.

In some embodiments, the container is entirely formed from any of the linear polymers as described above.

In some embodiments, the inner surface has a smoothness adapted so as not to form a precipitation or crystallisation site for $SnO_2$.

Without wishing to be bound by any theory, it is believed that mouthrinse solutions containing stannous ions in the Sn(II) oxidation state (such as in stannous fluoride, $SnF_2$) are prone to oxidation from the lower Sn(II) oxidation state to the higher Sn(IV) oxidation state. It is believed that the tin as Sn(IV) can be present as partly water-soluble $Sn^{4+}$-hydroxo complexes (e.g. simplified as $Sn(OH)_4$ or, in a more complicated formulation as $[Sn(OH)_6]^{2-}$—$SnF_2^{2+}$), or as water-insoluble and therefore dispersed and/or precipitated stannic oxide, $SnO_2$.

Again without wishing to be bound by any theory, it is believed that, although the therapeutic effect of $Sn^{2+}$ ions dissolved in aqueous solution is significantly higher than the therapeutic effect of the water-soluble Sn(IV) complexes (such as the $Sn(OH)_4$ and $[Sn(OH)_6]^{2-}$—$SnF_2^{2+}$ complexes), the water-soluble Sn(IV) complexes still have a useful therapeutic effect in such solutions. However, it is believed that the precipitated water-insoluble stannic oxide $SnO_2$ has little or no direct therapeutic effect.

The present inventors have surprisingly found that the use of the linear polymers as defined above as a primary container material for aqueous compositions comprising at least one water-soluble source of $Sn^{2+}$ ions (such as, for example, $SnF_2$) prevents the precipitation of water-insoluble $SnO_2$ (thought to be formed from water-soluble $Sn(OH)_4$), thus the composition remains clear after oxidation of Sn(II)

to Sn(IV) upon aging. However, the standard polyethylene terephthalate (PET) container material is not able to prevent the formation of insoluble stannic oxide, and stannic oxide precipitation is clearly observed when such compositions are packaged in standard polyethylene terephthalate (PET) containers.

The present inventors have observed that, when $Sn^{2+}$-containing compositions are packaged in a container formed from polypropylene, a higher concentration of the oxidised $Sn^{4+}$ can be maintained in solution than when the compositions are packaged in container formed from polyethylene terephthalate (PET), and the solutions packaged in polypropylene containers do not show the turbidity (believed to be caused by precipitation of insoluble $SnO_2$) which is observed when such solutions are packaged in PET containers. The present inventors observed that small polypropylene bottles containing 10 mL test samples of meridol® solution in which the Sn(II) was completely oxidised to Sn(IV) did not show any turbidity (caused by precipitation of insoluble $SnO_2$) after a storage time of several years. The concentration of soluble Sn(IV) measured after centrifugation after a storage time of 3 years was 396 ppm, i.e. close to target of 400 ppm, therefore no $SnO_2$ was precipitated.

Without wishing to be bound by any theory, it is believed that this phenomenon may be explained by essential chemical differences between the PET container material and the polypropylene container material. The structures of polypropylene and PET are shown below:

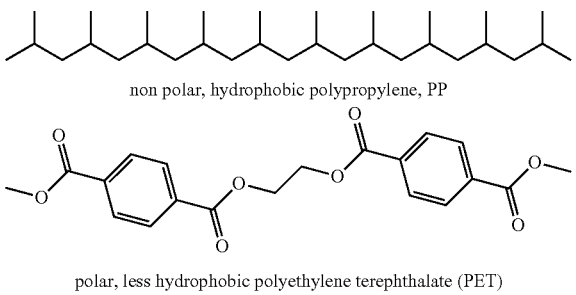

non polar, hydrophobic polypropylene, PP polar, less hydrophobic polyethylene terephthalate (PET)

The polypropylene container material has an overall low polarity, which is thought to be caused by the relatively low electronegativity of the constituent atoms of the polymer, and also by the simple linear structure of the polymer.

In contrast, polyethylene terephthalate (PET) comprises aliphatic and aromatic structures together with polar ester groups, and has a higher polarity than that of polypropylene. Again without wishing to be bound by any theory, the higher electronegativity of the constituent atoms of PET is thought to be sufficient to enhance the crystallisation process of insoluble stannic oxide ($SnO_2$) on the polymer surface after a certain induction time, therefore resulting in turbid solutions.

It is thought that the more polar PET material allows for the formation of small crystals of stannic oxide, which then propagate a precipitation of larger amounts of stannic oxide (for example as Cassiterite) after a longer storage time.

It is also thought that other polymers with a similar linear structure to that of polypropylene could also be used in the present invention e.g. polyethylene, polyvinylchloride, polyacrylonitrile.

Without wishing to be bound by any theory, it is also thought that the roughness of the polymer surface may also contribute to this effect or to the rate of precipitation of $SnO_2$ from the water-soluble Sn(IV) complex $Sn(OH)_4$.

Deposition of $SnO_2$ occurs on the rough polymer surface. This may favour a further and continuous precipitation of stannic oxide ($SnO_2$).

A smooth polymer surface has a much smaller surface area than that of a rough surface. There is therefore much less interaction between dissolved species and a smooth surface than between dissolved species and a rough surface. Therefore, the precipitation of stannic oxide ($SnO_2$) is reduced when the surface is smooth as opposed to rough.

Evidence for the contribution of surface roughness of the polymer material is also shown in the Examples, below.

EXAMPLES

Contribution of Surface Roughness

A commercially available mouthrinse ("Mouthrinse") concentrate containing 12,000 ppm Sn(II) was diluted with water in the ratio Mouthrinse concentrate:water of 1:30. This diluted solution was filled into six polypropylene sample bottles of each about 12 mL volume. After the dilution of the Mouthrinse with water at the ratio of 1:30, the concentration of Sn(II) in each sample was 400 ppm.

Seven strips of identical polypropylene bottle material were added to each of these six sample bottles. The strips of material were scratched and roughened using scissors before insertion into the polypropylene bottles. The effect of the manual scratching with the scissors was clearly visible. It was thought that a rough surface might act as a possible trigger for introduction and acceleration of micro- or nano-crystallisation of water-insoluble $SnO_2$.

As a control, the Mouthrinse concentrate diluted as described above was added to six polypropylene sample bottles of each about 12 mL volume, but no roughened polypropylene strips were added to these samples. It was thought that these solutions might remain clear or significantly less turbid due to a reduction in or absence of precipitated $SnO_2$.

The samples were closed with a polyethylene foil, but with full contact to air in order to promote the oxidation of Sn(II) and the precipitation process of stannic oxide ($SnO_2$) with the effect of increasing turbidity of the solution. The samples were closed with the foil only to prevent any spill or some loss of liquid during the test of 15 days. This closing was deliberately not done as an air-tight seal, as the presence of air during the test was necessary to promote the oxidation of Sn(II). It was thought that the samples with roughened strips might show insoluble precipitated $SnO_2$, whereas the samples without roughened strips might form water-soluble Sn(IV) oxides with no $SnO_2$ precipitation i.e. clear solutions.

The solutions were studied after a time of 15 days, using the measurement of the colour values L*, a*, b* as a suitable measure for the turbidity. L*a*b*-values are international values for colour measurement. The CIE-Lab (Commission Internationale de l'eclairage) colour system is based on these three parameters: L* (brightness), a* (red-green), b* (yellow-blue). The brightness L* also provides a measure of turbidity or opalescence, because of scattering the incident light-beam. Among these colour values, it is mainly the L*-factor which is correlated to the turbidity of a solution, because of the scattering of the incident light by the dispersed stannic oxide particles during the measurement. This light-scattering decreases the L*-value by a diffuse light-reflection.

During the storage time of 15 days, the samples with the solution were in full contact with oxygen in the air (as the samples were not closed so as to be air-tight, as discussed above).

After the 15 days, the solutions from each of the six sample bottles which had seven strips of roughened polypropylene bottle material inserted therein were carefully poured into suitable measuring cups for performance of L*a*b* measurements. The solutions from each of the above six sample bottles which did not have roughened strips of polypropylene bottle material inserted therein were also poured into suitable measuring cups for the performance of L*a*b* measurements. The L*a*b* values of each of these two series of six samples were measured. It was hypothesised that there may be a significant difference in the L*-value (which is known to be sensitive for turbidity or for opalescence) for the samples of these two series.

The L* value was measured nine times for each of the six solutions into which the strips of roughened polypropylene bottle material were inserted. For the six solutions into which no polypropylene strips were inserted, two of these solutions had their L* values measured nine times; two had their L* values measured eight times; and two had their L* values measured seven times. The mean L* values for each of the separate samples were then calculated, and are shown in Table 1, below:

TABLE 1

| Sample with roughened polypropylene strips | mean L* | Sample without roughened polypropylene strips | mean L* |
| --- | --- | --- | --- |
| 1 | 33.453 | 1 | 36.5414 |
| 2 | 35.056 | 2 | 38.8686 |
| 3 | 31.816 | 3 | 35.1513 |
| 4 | 33.196 | 4 | 34.6900 |
| 5 | 35.044 | 5 | 32.1056 |
| 6 | 34.980 | 6 | 36.0522 |
| Overall mean L* | 33.924 | Overall mean L* | 35.568 |
| STDEV | 1.330 | STDEV | 2.236 |
| CV % | 3.92 | CV % | 6.29 | t-Test: 0.15
F-test: 0.28

In the data in Table 1, above, the small difference in L* (ΔL*=1.644 units) shows, in the statistical t-test, a probability of error of about 15% (or a statistical certainty of 85%) because of the low number of degrees of freedom (6+6−2=10). The statistical t-test is also known as Student's-t-test, and is a statistical procedure comparing the mean values and the standard deviations together with the total degree of freedom (the total degree of freedom being the sum of the number of measurement of the first mean-value, e.g. $n_1$, and the number of measurement of the second mean-value $n_2$).

The above data shows, by the L* values of the samples with the scratched, roughened strips being smaller than the L* values of the samples without scratched, roughened strips, that there is a trend towards a somewhat higher turbidity of the samples which were in contact with the roughened surfaces as compared to those samples which were not in contact with a roughened surface.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

The invention claimed is:

1. A packaged aqueous oral care composition comprising a container and a composition wherein the composition comprises at least one water-soluble source of $Sn^{2+}$ ions and wherein the container comprises an inner surface at least partially formed from a linear polymer, wherein the linear polymer is a homopolymer or a copolymer of monomers having the structure:

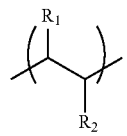

wherein $R_1$ and $R_2$ are the same or different and are independently selected from a hydrogen atom, an alkyl group, an alkenyl group, a halogen atom and a nitrile group; and wherein the composition is a mouthrinse.

2. The oral care composition of claim 1, wherein the inner surface has a smoothness adapted so as not to form a precipitation or crystallisation site for $SnO_2$.

3. The oral care composition of claim 1, wherein the halogen atom is a chlorine atom.

4. The oral care composition of claim 1, wherein the alkyl group is a $C_1$-$C_{10}$ alkyl group, optionally wherein the alkyl group is a $C_3$-$C_8$ alkyl group.

5. The oral care composition of claim 4, wherein the alkyl group is a methyl group, an ethyl group, a propyl group, a butyl group, a pentyl group or a hexyl group.

6. The oral care composition of claim 1, wherein the alkenyl group is a $C_2$-$C_{10}$ alkenyl group, optionally wherein the alkenyl group is a $C_4$-$C_8$ alkenyl group.

7. The oral care composition of claim 1, wherein $R_1$ is a hydrogen atom.

8. The oral care composition of claim 1, wherein the polymer is a homopolymer or copolymer of one or more olefins.

9. The oral care composition of claim 8, wherein the polymer is polypropylene.

10. The oral care composition of claim 8, wherein the polymer is polyethylene.

11. The oral care composition of claim 8, wherein the polymer is polyvinylchloride.

12. The oral care composition of claim 8, wherein the polymer is polyacrylonitrile.

13. The oral care composition of claim 1, wherein the $Sn^{2+}$ ions are present in the composition in a concentration of from 100 ppm to 12,000 ppm.

14. The oral care composition of claim 13, wherein the $Sn^{2+}$ ions are present in the composition in a concentration of from 400 ppm to 6,000 ppm.

15. The oral care composition of claim 14, wherein the $Sn^{2+}$ ions are present in the composition in a concentration of from 700 ppm to 4,000 ppm.

16. The oral care composition of claim 15, wherein the $Sn^{2+}$ ions are present in the composition in an amount of from 1,000 ppm to 2,000 ppm.

17. The oral care composition of claim 1, wherein the source of $Sn^{2+}$ ions comprises $SnCl_2$.

18. The oral care composition of claim 1, wherein the source of $Sn^{2+}$ ions comprises $SnF_2$.

19. The oral care composition of claim 1, wherein the composition further comprises an amine fluoride.

20. The oral care composition of claim 19, wherein the amine fluoride is N'-octadecyltrimethylendiamine-N,N,N'-tris(2-ethanol)-dihydrofluoride.

21. The oral care composition of claim 18, wherein the total concentration of F⁻ ions in the oral care composition is from 150 ppm to 5,000 ppm.

22. The oral care composition of claim 21, wherein the total concentration of F⁻ ions present in the composition is from 200 ppm to 1,500 ppm.

23. The oral care composition of claim 1, further comprising one or more agents selected from diluents, bicarbonate salts, pH modifying agents, surfactants, foam modulators, thickening agents, viscosity modifiers, humectants, sweeteners, flavorants, pigments, antibacterial agents, anticaries agents, anticalculus or tartar control agents, and mixtures thereof.

24. The oral care composition of claim 1, wherein the composition is free of abrasives.

25. The oral care composition of claim 1, wherein the composition comprises greater than 90 wt % water.

26. The oral care composition of claim 1, wherein the composition has a pH of from 3 to 7.

27. The oral care composition of claim 1, wherein the composition has a pH of from 4 to 5.

28. A method of preventing the formation of insoluble $SnO_2$ in an aqueous composition comprising at least one water-soluble source of $Sn^{2+}$ ions, the method comprising packaging the aqueous composition in a container having an inner surface, wherein the inner surface is at least partially formed from a linear polymer, wherein the linear polymer is a homopolymer or a copolymer of monomers having the structure:

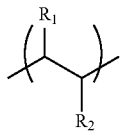

wherein $R_1$ and $R_2$ are the same or different and are independently selected from a hydrogen atom, an alkyl group, an alkenyl group, a halogen atom and a nitrile group; wherein the composition is an oral care composition which is a mouthrinse.

29. The method of claim 28, wherein the inner surface has a smoothness adapted so as not to form a precipitation or crystallisation site for $SnO_2$.

30. The method of claim 28, wherein the halogen atom is a chlorine atom.

31. The method of claim 28, wherein the alkyl group is a $C_1$-$C_{10}$ alkyl group, optionally wherein the alkyl group is a $C_3$-$C_8$ alkyl group.

32. The method of claim 31, wherein the alkyl group is a methyl group, an ethyl group, a propyl group, a butyl group, a pentyl group or a hexyl group.

33. The method of claim 28, wherein the alkenyl group is a $C_2$-$C_{10}$ alkenyl group, optionally wherein the alkenyl group is a $C_4$-$C_8$ alkenyl group.

34. The method of claim 28, wherein $R_1$ is a hydrogen atom.

35. The method of claim 28, wherein the polymer is a homopolymer or copolymer of one or more olefins.

36. The method of claim 35, wherein the polymer is polypropylene.

37. The method of claim 35, wherein the polymer is polyethylene.

38. The method of claim 35, wherein the polymer is polyvinylchloride.

39. The method of claim 35, wherein the polymer is polyacrylonitrile.

40. The method of claim 28, wherein the $Sn^{2+}$ ions are present in the composition in a concentration of from 100 ppm to 12,000 ppm.

41. The method of claim 40, wherein the $Sn^{2+}$ ions are present in the composition in a concentration of from 400 ppm to 6,000 ppm.

42. The method of claim 41, wherein the $Sn^{2+}$ ions are present in the composition in a concentration of from 700 ppm to 4,000 ppm.

43. The method of claim 42, wherein the $Sn^{2+}$ ions are present in the composition in an amount of from 1,000 ppm to 2,000 ppm.

44. The method of claim 28, wherein the source of $Sn^{2+}$ ions comprises $SnCl_2$.

45. The method of claim 28, wherein the source of $Sn^{2+}$ ons comprises $SnF_2$.

46. The method of claim 28, wherein the composition further comprises an amine fluoride.

47. The method of claim 46, wherein the amine fluoride is N'-octadecyltrimethylendiamine-N,N,N'-tris(2-ethanol)-dihydrofluoride.

48. The method of claim 45, wherein the total concentration of F⁻ ions in the composition is from 150 ppm to 5,000 ppm.

49. The method of claim 48, wherein the total concentration of F⁻ ions present in the composition is from 200 ppm to 1,500 ppm.

50. The method of claim 28, wherein the composition further comprises one or more agents selected from diluents, bicarbonate salts, pH modifying agents, surfactants, foam modulators, thickening agents, viscosity modifiers, humectants, sweeteners, flavorants, pigments, antibacterial agents, anticaries agents, anticalculus or tartar control agents, and mixtures thereof.

51. The method of claim 28, wherein the composition is free of abrasives.

52. The method of claim 28, wherein the composition comprises greater than 90 wt % water.

53. The method of claim 28, wherein the composition has a pH of from 3 to 7.

54. The method of claim 28, wherein the composition has a pH of from 4 to 5.

55. The oral care composition of claim 1, wherein the container is a bottle, a tube, a vial, a cartridge, a pump-action dispensing container.

56. The method of claim 28, wherein the container is a bottle, a tube, a vial, a cartridge, a pump-action dispensing container.

* * * * *